United States Patent
Ishinabe (10) Patent No.: US 10,568,504 B2
(45) Date of Patent: Feb. 25, 2020

(54) OPHTHALMOLOGIC APPARATUS (71) Applicant: TOPCON CORPORATION, Itabashi-ku (JP)

(72) Inventor: Ikuo Ishinabe, Saitama (JP)

(73) Assignee: TOPCON CORPORATION, Tokyo (JP)

( * ) Notice: Subject to any disclaimer, the term of this patent is extended or adjusted under 35 U.S.C. 154(b) by 14 days.

(21) Appl. No.: 15/786,092

(22) Filed: Oct. 17, 2017

(65) Prior Publication Data

US 2018/0116502 A1 May 3, 2018

(30) Foreign Application Priority Data

Oct. 31, 2016 (JP) .................. 2016-213214

(51) Int. Cl.
| | | |
|---|---|---|
| *A61B 3/10* | (2006.01) | |
| *A61B 3/12* | (2006.01) | |
| *A61B 3/00* | (2006.01) | |
| *A61B 3/117* | (2006.01) | |
| *A61B 3/14* | (2006.01) | |

(52) U.S. Cl.
CPC ............ *A61B 3/102* (2013.01); *A61B 3/0008* (2013.01); *A61B 3/1025* (2013.01); *A61B 3/117* (2013.01); *A61B 3/12* (2013.01); *A61B 3/14* (2013.01)

(58) Field of Classification Search
CPC ........... A61B 3/00; A61B 3/0008; A61B 3/10; A61B 3/1005; A61B 3/102; A61B 3/1025; A61B 3/113; A61B 3/12
See application file for complete search history.

(56) References Cited

U.S. PATENT DOCUMENTS

| | | | |
|---|---|---|---|
| 2012/0242955 A1 | 9/2012 | Yoshino et al. | |
| 2014/0139804 A1* | 5/2014 | Ehrmann | A61B 3/14 351/205 |
| 2014/0211157 A1* | 7/2014 | Nakahara | A61B 3/102 351/206 |
| 2014/0300863 A1 | 10/2014 | Fukuma et al. | |
| 2014/0300864 A1 | 10/2014 | Fukuma et al. | |
| 2014/0300866 A1 | 10/2014 | Fukuma et al. | |
| 2014/0320809 A1 | 10/2014 | Fukuma et al. | |
| 2014/0320810 A1 | 10/2014 | Fukuma et al. | |
| 2015/0085252 A1 | 3/2015 | Fujimura et al. | |
| 2015/0141972 A1* | 5/2015 | Woodley | A61B 3/102 606/5 |
| 2016/0345822 A1 | 12/2016 | Fujimura et al. | |

FOREIGN PATENT DOCUMENTS

| | | |
|---|---|---|
| JP | 2012-196324 | 10/2012 |
| JP | 2013-248376 | 12/2013 |
| JP | 2014-200678 | 10/2014 |
| JP | 2014-200679 | 10/2014 |
| JP | 2014-200680 | 10/2014 |

* cited by examiner

Primary Examiner — Robert E. Tallman
(74) Attorney, Agent, or Firm — Xsensus, LLP (57) ABSTRACT An ophthalmologic apparatus according to some embodiments comprise an objective lens, a data acquisition system, and an anterior segment photographing system. The data acquisition system is configured to acquire data of a subject's eye optically via the objective lens. The anterior segment photographing system includes a pair of optical systems for photographing an anterior segment of the subject's eye from different directions via the objective lens.

7 Claims, 6 Drawing Sheets

OPHTHALMOLOGIC APPARATUS

CROSS-REFERENCE TO RELATED APPLICATION

This application is based upon and claims the benefit of priority from Japanese Patent Application No. 2016-213214, filed Oct. 31, 2016; the entire contents of which are incorporated herein by reference.

BACKGROUND

Types of ophthalmologic apparatuses include ophthalmologic imaging apparatuses for obtaining images of a subject's eye, ophthalmologic measuring apparatuses for measuring characteristics of a subject's eye, and the like.

Examples of the ophthalmologic imaging apparatus include an optical coherence tomography (OCT) apparatus using OCT, a fundus camera, a scanning laser ophthalmoscope (SLO), a slit lamp, and the like. Examples of the ophthalmologic measuring apparatuses include a subject's eye refraction test apparatus (refractometer, keratometer), a tonometer, a specular microscope, a wavefront analyzer, and the like. Besides, types of ophthalmologic apparatuses include an ophthalmic surgical microscope, an ophthalmologic laser photocoagulator, and the like.

In ophthalmic examinations and ophthalmic treatments (including ophthalmic surgeries) using these apparatuses, it is required to grasp a state of an anterior segment of the subject's eye in detail. Various types of methods for grasping such the state of the anterior segment are suggested. For example, Japanese Unexamined Patent Application Publication No. 2012-196324 discloses a fundus camera including an anterior segment observing system for observing the anterior segment of the subject's eye.

SUMMARY

An ophthalmologic apparatus according to one aspect of the embodiment comprise an objective lens, a data acquisition system, and an anterior segment photographing system. The data acquisition system is configured to acquire data of a subject's eye optically via the objective lens. The anterior segment photographing system includes a pair of optical systems for photographing an anterior segment of the subject's eye from different directions via the objective lens.

DESCRIPTION OF THE EMBODIMENTS

In the ophthalmic examinations, by grasping the state of the anterior segment of the subject's eye in detail and adjusting position(s) between an optical system of the apparatus and the subject's eye, precision and accuracy of the examinations can be improved. In the ophthalmic treatments, by grasping the state of the anterior segment of the subject's eye in detail, it becomes possible to apply more advanced treatment to the subject's eye. That is, in the ophthalmic examinations and the ophthalmic treatments, grasping the anterior segment of the subject's eye in detail is important.

According to some embodiments, a novel technique to grasp an anterior segment of a subject's eye in detail can be provided.

Some exemplary embodiments of the ophthalmologic apparatus will be described in detail with reference to the drawings. Any of the contents of the documents cited in the present specification and arbitrary known techniques may be applied to the embodiments below.

An ophthalmologic apparatus according to some embodiments includes an anterior segment photographing system at least, and the ophthalmologic apparatus is capable of photographing an anterior segment of a subject's eye. Such a configuration can be applied to any ophthalmologic apparatus including the anterior segment photographing system. Ophthalmologic apparatuses having an anterior segment observing system or the anterior segment photographing system include ophthalmologic imaging apparatuses, ophthalmologic measuring apparatuses, and the like.

Examples of ophthalmologic imaging apparatuses include an optical coherence tomography (OCT) apparatus that obtains cross sectional images using OCT, a fundus camera that photographs a fundus, a scanning laser ophthalmoscope (SLO) that obtains images of a fundus by laser scanning with a confocal optical system, a slit lamp that obtains images by photographing an optical section of a cornea using slit light, and the like.

Examples of the ophthalmologic measuring apparatuses include a subject's eye refraction test apparatus (refractometer, keratometer) for measuring the refractive properties of the subject's eye, a tonometer, a specular microscope for obtaining the properties of the cornea (corneal thickness, cell distribution, etc.), a wavefront analyzer for obtaining the aberration information of the subject's eye by using a Hartmann-Shack sensor, and the like.

In some embodiments, the ophthalmologic apparatus includes an anterior segment observing system for observing the anterior segment of the subject's eye. The ophthalmologic apparatuses including the anterior segment observing system like this include an ophthalmic surgical microscope for observing a predetermined site of the subject's eye during surgery, an ophthalmologic laser photocoagulator for irradiating a predetermined tissue of the subject's eye with laser light, and the like. Besides, in some embodiments, the ophthalmologic apparatus also includes an apparatus having a function combining a function of SLO and a function of OCT, and the like. Hereinafter, cases in which an ophthalmologic apparatus according to some embodiments is applied to an ophthalmologic photographing apparatus including an anterior segment photographing system and having a function of SLO and a function of OCT will be described.

In the following description, the left/right direction viewed from a subject is regarded as the X direction, the up/down direction is regarded as the Y direction, and the depth direction of an optical system viewed from the subject is regarded as the Z direction.

[Optical System]

Figure 1:
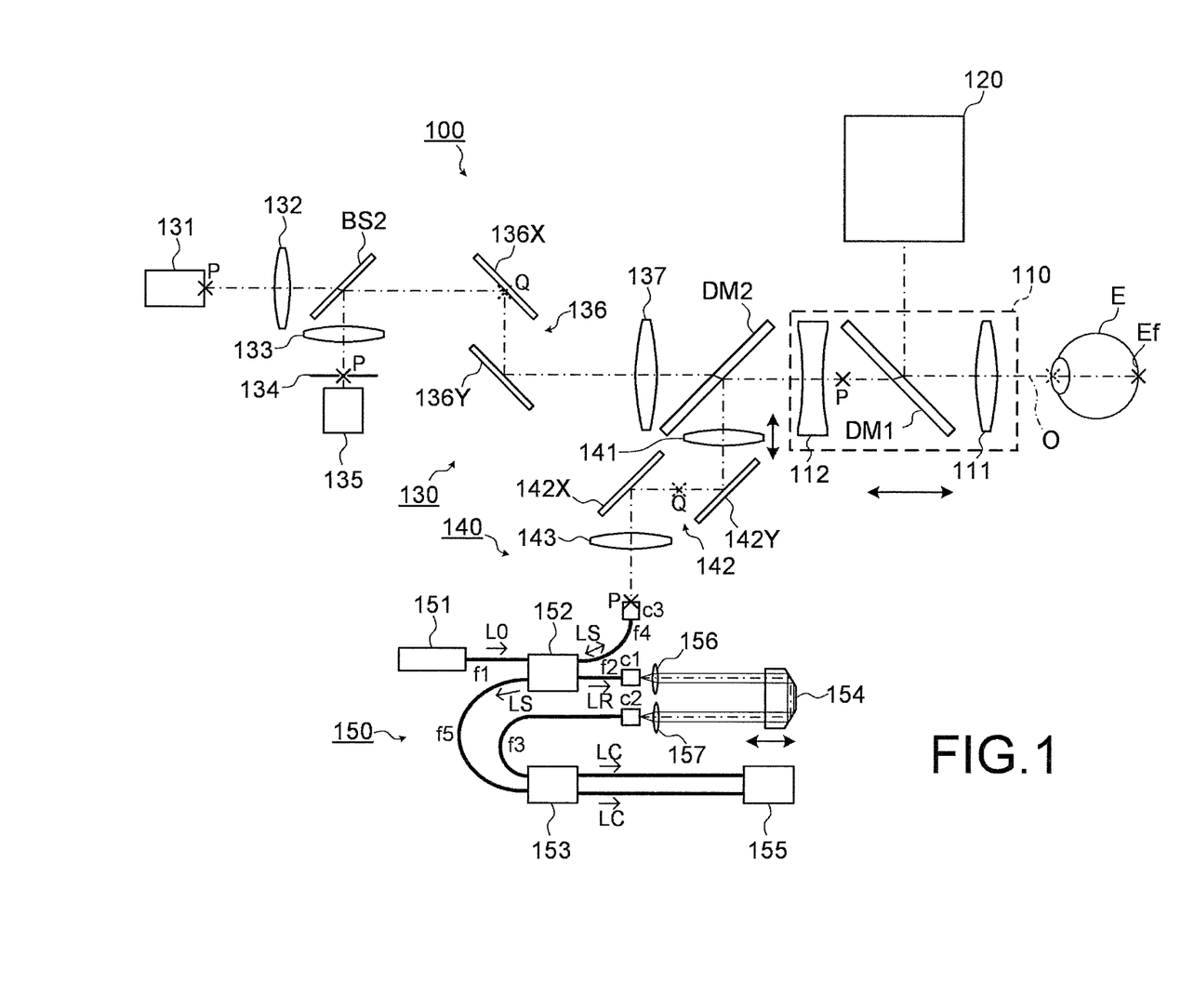
FIG. 1 is a schematic diagram illustrating an example of the configuration of an optical system of an ophthalmologic apparatus according to embodiments.
Figure 2:
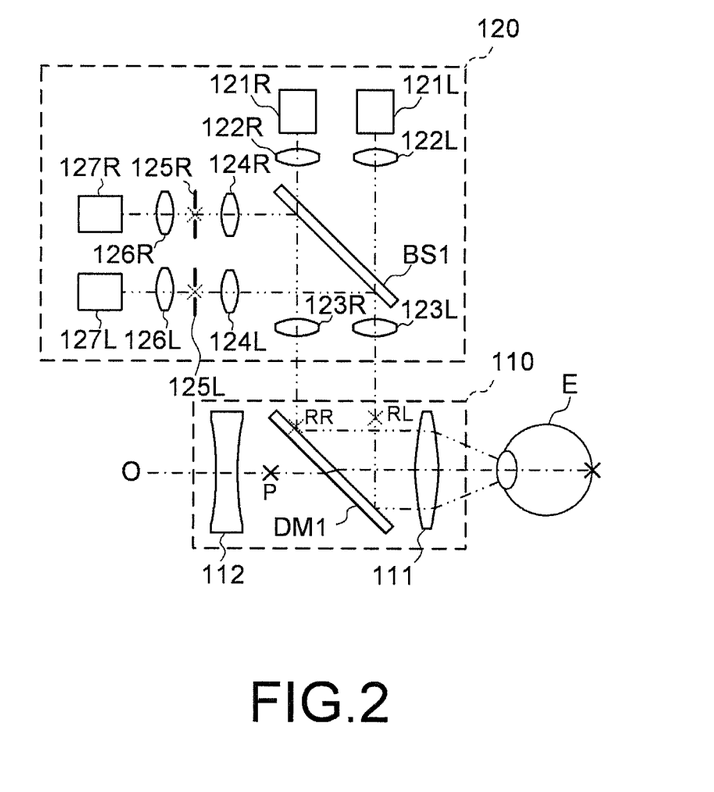
FIG. 2 is a schematic diagram illustrating an example of the configuration of an optical system of an ophthalmologic apparatus according to the embodiments.

FIGS. 1 and 2 illustrate an example of the configuration of the optical system of the ophthalmologic apparatus according to some embodiments. FIG. 1 shows an example of the configuration of the optical system of the ophthalmologic apparatus. FIG. 2 shows an example of the configuration of the optical system of the anterior segment photographing system of FIG. 1. In FIG. 2, like reference numerals designate like parts as in FIG. 1. The same description may not be repeated. In FIGS. 1 and 2, a position optically conjugate with a fundus Ef of the subject's eye E or near the position is illustrated as a fundus conjugate position P, and a position optically conjugate with a pupil of the subject's eye E or near the position is illustrated as a pupil conjugate position Q.

An optical system 100 includes a projection system that projects light onto the subject's eye E via an objective lens system 110 and a light receiving system that receives return light of the light projected onto the subject's eye by the projection system via the objective lens system 110. The ophthalmologic apparatus forms an image based on the detection result obtained by the light receiving system. In some embodiments, the ophthalmologic apparatus forms an SLO image and an OCT image. That is, the optical system 100 includes an SLO optical system 130 and an OCT optical system 140. The SLO optical system 130 includes an SLO projection system and an SLO light receiving system. The OCT optical system 140 includes an OCT projection system and an OCT light receiving system.

The ophthalmologic apparatus is provided with an anterior segment photographing system 120 for photographing the anterior segment of the subject's eye. The optical system 100 is movable with the objective lens system 110 and the anterior segment photographing system 120 in the X direction, the Y direction, and the Z direction by means of a moving mechanism (not illustrated, a moving mechanism 100D to be hereinafter described). The moving mechanism moves the optical system 100 etc. based on image(s) of the anterior segment of the subject's eye E, thereby the ophthalmologic apparatus can perform alignment for the position matching of the optical system 100 with respect to the subject's eye E. Hereinafter, cases in which the optical system 100 includes the objective lens system 110 and the anterior segment photographing system 120 will be described. However, the optical system 100 may not include these.

(Objective Lens System)

The objective lens system 110 includes an objective lens 111. In some embodiments, the objective lens 111 includes two or more lenses. The objective lens system 110 according to some embodiments includes two or more lenses. A dichroic mirror DM1 is arranged between (among) the two or more lenses. For example, the objective lens system 110 may be a lens unit (Nagler type) including the objective lens 111 and a concave lens 112. The objective lens 111 and the concave lens 112 are arranged in this order from the subject's eye E. The dichroic mirror DM1 is an optical path coupling member to couple an optical path of the anterior segment photographing system 120 with both of an optical path of the SLO optical system 130 and an optical path of the OCT optical system 140. The fundus conjugate position P which is the position optically conjugate with the fundus (the retina) of the subject's eye E or near the position is arranged between the dichroic mirror DM1 and the concave lens 112. The objective lens system 110 may include the dichroic mirror DM1.

The dichroic mirror 1 transmits light (SLO light) from the SLO optical system 130, return light of the SLO light from the subject's eye E, light (OCT light, measurement light) from the OCT optical system 140, and return light of the OCT light from the subject's eye E. The dichroic mirror DM1 reflects light from the anterior segment photographing system 120 toward the subject's eye E, and also reflects return light from the subject's eye E toward the anterior segment photographing system 120, the return light being return light of the light from the anterior segment photographing system 120.

In some embodiments, the objective lens system 110 includes a plurality of objective lens units which are capable of selectively arranging in an optical axis O of the optical system 100 depending on photographing modes with different image ranges each other. The photographing modes include a wide-angle photographing mode for photographing the subject's eye E with a first range (e.g., the angle of view of 100 degrees) and a high magnification photographing mode for imaging the subject's eye E with a second range (e.g., the angle of view of 50 degrees) which is narrower than the first range. In the wide-angle photographing mode, a wide-angle image (SLO image or OCT image) which shows the first range of the subject's eye E is obtained. In the high magnification photographing mode, a high magnification (narrow angle) image (SLO image or OCT image) which shows the second range of the subject's eye. The second range is narrower than the; first range. The plurality of objective lens units are selectively arranged in the optical axis O by manually or automatically using a known rotating mechanism or a sliding mechanism depending on the photographing mode, for example.

The objective lens system 110 is movable along the optical axis O by means of a moving mechanism (not illustrated, a moving mechanism 110D to be hereinafter described). As a result, it is possible to move the objective lens system 110 with respect to the optical system 100 in the Z direction. Therefore, both of a focus position of the SLO optical system 130 and a focus position of the OCT optical system 140 is changed.

(Anterior Segment Photographing System)

As shown in FIG. 2, the anterior segment photographing system 120 includes a pair of optical systems for photographing the anterior segment of the subject's eye E from different directions. One of the pair of optical systems is provided with an anterior segment illumination light source 121L, a collimator lens 122L, relay lenses 123L and 124L, a diaphragm (aperture stop) 125L, an imaging lens 126L, and an anterior segment photographing camera 127L. The other of the pair of optical systems is provided with an anterior segment illumination light source 121R, a collimator lens 122R, relay lenses 123R and 124R, a diaphragm (aperture stop) 125R, an imaging lens 126R, and an anterior segment photographing camera 127R. The pair of the optical systems are provided with a beam splitter for dividing into illumination light and return light of the illumination light. In FIG. 2, a beam splitter BS1 common to the pair of optical systems is arranged. The beam splitter BS1 is an optical path coupling member to couple an optical path of the return light of the illumination light for illuminating the anterior segment of the subject's eye E with an optical path of the illumination light. Each of the pair of optical systems has the same configuration. Therefore, one of the pair of optical systems is explained.

By changing position or size of the opening of the diaphragm 125L or 125R, brightness, contrast, and the like can be changed. In this embodiment, each of the diaphragm 125L and 125R is arranged at a position obtained a desired field of view within an effective lens diameter of the objective lens 111 in the optical path of the return light of the illumination light from the subject's eye E.

A relay optical system composed of the relay lenses 123L and 124L forms an optical conjugate point RL of the diaphragm 125L (opening) between the objective lens 111 and the diaphragm 125L. Similarly, a relay optical system composed of the relay lenses 123R and 124R forms an optical conjugate point RR of the diaphragm 125R (opening) between the objective lens 111 and the diaphragm 125R. In this embodiment, at least one of the conjugate points RL and RR is located in the vicinity of an optical path coupling surface of the dichroic mirror DM1.

The anterior segment illumination light source 121L (121R) is a light source for illuminating the anterior segment of the subject's eye E. The anterior segment photographing camera 127L (127R) includes an imaging device to detect reflection light (return light) from the anterior segment of the subject's eye E illuminated by the anterior segment illumination light source 121L (121R). An LED emitting near-infrared light is used as the anterior segment illumination light source 121L (121R). The light emitted from the anterior segment illumination light source 121L (121R) is collimated into a parallel light flux by the collimator lens 122L (122R). The illumination light collimated into the parallel light flux passes through the beam splitter BS1. After passing through the beam splitter BS1, the illumination light is deflected toward the subject's eye E by the dichroic mirror DM1.

The return light of the illumination light from the subject's eye E passes through the objective lens 111. The return light passing through the objective lens 111 is reflected by the dichroic mirror DM1. The return light reflected by the dichroic mirror DM1 passes through the relay lens 123L (123R). The return light passing through the relay lens 123L (123R) is reflected by the beam splitter BS1. The return light reflected by the beam splitter BS1 is guided to the relay lens 124L (124R). The return light of the illumination light guided to the relay lens 124L (124R) passes through the relay lens 124L (124R). The return light passing through the relay lens 124L (124R) passes through the opening formed in the diaphragm 125L (125R). The return light passing through the opening formed in the diaphragm 125L (125R) is condensed on a detector plane (an imaging surface) of the imaging device in the anterior segment photographing camera 127L (127R) by means of the imaging lens 126L (126R). For example, the detector plane of the imaging device is arranged at the pupil conjugate position Q. Besides, the detector plane of the imaging device may be arranged at an anterior segment conjugate position which is a position optically conjugate with the anterior segment of the subject's eye E or near the position. In some embodiments, the anterior segment conjugate position almost coincides with the pupil conjugate position Q. The imaging device in the anterior segment photographing camera 127L (127R) includes a charge-coupled device (CCD) or a complementary metal-oxide semiconductor (CMOS) image sensor, for example. The result of the detection of the return light from the anterior segment of the subject's eye E obtained by the imaging device in the anterior segment photographing camera 127L (127R) is used for forming an image of the anterior segment.

In some embodiments, a position between the objective lens 111 and the relay lens 123L (123R) is a position optically conjugate with the diaphragm 125L (125R). Thereby, it becomes possible to arrange the pair of optical systems side by side, while relaying the conjugate point by means of the relay lenses 123L (123R) and 124L (124R) with small lens diameters. The pair of the optical systems are used for imaging the anterior segment of the subject's eye E from different directions. This makes it enable to secure a sufficient field of vision regarding to each of the pair of optical systems. In addition, because it becomes possible to secure the stereo angle sufficiently, observing the anterior segment of the subject's eye E with natural stereoscopic effect similar to that observed with the naked eye becomes possible.

In particular, in the case that the objective lens 111 is a wide-angle lens whose focal distance is short, the working distance (WD) which is a distance between the subject's eye E and the objective lens 111 becomes shorter. Thereby, it is difficult to arrange a photographing apparatus for stereoscopic imaging of the anterior segment of the subject's eye E. On the other hand, according to some embodiments, it becomes possible to photograph the anterior segment of the subject's eye E with the pair of optical systems from different directions, while securing field of vision with the diaphragm 125L (125R) by relaying the conjugate points of diaphragm 125L (125R) in the vicinity of the optical path coupling surface of the dichroic mirror DM1 by means of the relay lenses 123L (123R) and 124L (124R).

(SLO Optical System)

As shown in FIG. 1, the optical path of the SLO optical system 130 and the optical path of the OCT optical system 140 are coupled by a dichroic mirror DM2. At least part of the SLO optical system 130 is formed as a telecentric optical system. Similarly, at least part of the OCT optical system 140 is formed as a telecentric optical system. The dichroic mirror DM2 coupled an optical path formed by the telecentric optical system of the SLO optical system 130 with an optical path formed by the telecentric optical system of the OCT optical system 140. Thereby, an aberration of a pupil (e.g., an exit pupil by the objective lens system 110) becomes small even if the focus position of the optical system 100 is changed by moving the objective lens system 110. Therefore, it becomes easy to adjust a focus state.

The SLO optical system 130 includes an SLO light source 131, a collimator lens 132, a beam splitter BS2, a condenser lens 133, a confocal diaphragm 134, a detector 135, an optical scanner 136, and a lens 137. The beam splitter BS2 is an optical path coupling member to couple an optical path of the return light of the SLO light projected onto the subject's eye E with an optical path of the SLO light.

The SLO light source 131 emits a laser beam having a center wavelength of 840 nm, for example. Examples of the SLO light source 131 include a laser diode (LD), a super-luminescent diode (SLD), a laser-driven light source (LDLS), or the like. The SLO light source 131 is arranged at the fundus conjugate position P.

Light emitted from the SLO light source 131 is collimated into a parallel light flux by a collimator lens 132. The light collimated into the parallel light flux passes through the beam splitter BS2. After passing through the beam splitter BS2, the light is deflected by the optical scanner 136. The optical scanner 136 is used to scan the fundus Ef of the subject's eye E with the light from the SLO light source 131. The optical scanner 136 includes an optical scanner 136X configured to deflect the light in the X direction and an optical scanner 136Y configured to deflect the light in the Y direction. The optical scanner 136X is a mirror whose tilt angle is variable. The tilt of the reflecting surface of the mirror is controlled by a controller 200 (described later). The optical scanner 136X is used for, for example, vertical scanning in the fundus plane. The optical scanner 136Y is located on the subject's eye E side of the optical scanner 136X. The optical scanner 136Y is a mirror whose tilt angle is variable. The tilt of the reflecting surface of the mirror is controlled by the controller 200. The optical scanner 136Y is used for, for example, horizontal scanning in the fundus plane perpendicular to the vertical direction. Either one of the optical scanner 136X and the optical scanner 136Y may be a low-speed scanner such as a galvano mirror, or the like and the other is a high-speed scanner such as a resonant mirror, a polygon mirror, a microelectromechanical systems (MEMS) mirror, or the like.

A reflective surface (deflected surface) of the optical scanner 136X is arranged at the pupil conjugate position Q. A reflective surface of the optical scanner 136Y is arranged at a position optically nonconjugate with the pupil of the subject's eye E. Thereby, an irradiation position of the light passing through the beam splitter BS2 on the reflective surface of the optical scanner 136Y moves when the tilt of the reflective surface of the optical scanner 136X is changed. That is, the SLO optical system 130 (the optical system 100) scans the fundus Ef with the light while a passage position in the plane perpendicular to the optical axis of the SLO optical system 130 at the pupil conjugate position Q. Therefore, by moving an incident position of the light in the pupil of the subject's eye E, an amount of the incident light per unit area at the pupil of the subject's eye E decreases compared to the case that the reflective surface of the optical scanner 136Y is arranged at the pupil conjugate position Q. In this way, by daring to generate the pupil aberration, the amount of the incident light per unit area decrease, and an amount of light capable of entering the eye can be increased. Incidentally, the pupil conjugate position Q may be arranged between the optical scanner 136X and the optical scanner 136Y. In this case, the pupil conjugate position Q may be arranged at an intermediate position between the optical scanner 136X and the optical scanner 136Y.

The lens 137 and the dichroic mirror DM2 are located on the subject's eye E side of the optical scanner 136Y. The light from the SLO light source 131 deflected by the optical scanner 136 passes through the lens 137, passes through the dichroic mirror DM2, and is projected onto the subject's eye E via the objective lens system 110.

The return light of the light from the SLO light source 131 projected onto the subject's eye E travels through the same optical path, and is reflected toward the detector 135 by the beam splitter BS2. The condenser lens 133 and the confocal diaphragm 134 are arranged between the beam splitter BS2 and the detector 135. The condenser lens 133 condenses the light reflected by the beam splitter BS2. The light condensed by the condenser lens 133 passes through an opening formed in the confocal diaphragm 134 and the light passing through the opening enters a detector plane of the detector 135. The opening formed in the confocal diaphragm 134 is arranged at the fundus conjugate position P. The detector 135 is made of, for example, an avalanche photodiode (APD) or a photomultiplier tube (PMT).

(OCT Optical System)

OCT optical system 140 includes a focusing lens 141, an optical scanner 142, a collimator lens 143, and an interference optical system 150. The interference optical system 150 includes an OCT light source 151, a fiber coupler 152, a fiber coupler 153, a prism 154, and a detector 155.

The focusing lens 141 is movable along an optical axis (an optical path) of the OCT optical system 140 by means of a moving mechanism (not illustrated, a moving mechanism 141D to be hereinafter described). Thereby, a focus position of the OCT optical system 140 can be changed independently of the SLO optical system 130. Therefore, it is possible to finely adjust a focus state of the OCT optical system 140 by moving the focusing lens 141 after adjusting a focus state of the SLO optical system 130 and the OCT optical system 140 by moving the objective lens system 110, for example.

The optical scanner 142 is used to scan the fundus Ef of the subject's eye E with a measurement light base on light from the OCT light source 151. The optical scanner 142 includes an optical scanner 142X configured to deflect the light in the X direction and an optical scanner 142Y configured to deflect the light in the Y direction. The optical scanner 142X is a mirror whose tilt angle is variable. The tilt of the reflecting surface of the mirror is controlled by a controller 200. The optical scanner 142X is used for, for example, horizontal scanning in the fundus plane. The optical scanner 142Y is located on the subject's eye E side of the optical scanner 142X. The optical scanner 142Y is a mirror whose tilt angle is variable. The tilt of the reflecting surface of the mirror is controlled by the controller 200. The optical scanner 142Y is used for, for example, vertical scanning in the fundus plane perpendicular to the horizontal direction. Either one of the optical scanner 142X and the optical scanner 142Y may be a low-speed scanner such as a low-speed galvano mirror, or the like and the other is a high-speed scanner such as a high-speed galvano mirror, or the like. An intermediate position between the optical scanner 142X and the optical scanner 142Y is arranged at the pupil conjugate position Q. The collimator lens 143 is located on the OCT light source 151 side of the optical scanner 142Y.

That is, the reflective surface of the optical scanner 142Y is arranged at a position optically nonconjugate with the pupil of the subject's eye E. Thereby, an irradiation position of the light (a measurement light LS describe later) passing through the collimator lens 143 on the reflective surface of the optical scanner 142Y moves when the tilt of the reflective surface of the optical scanner 142X is changed. More specifically, the OCT optical system 140 scans the fundus Ef with the light while a passage position in the plane perpendicular to the optical axis of the OCT optical system 140 at the pupil conjugate position Q. Therefore, by moving an incident position of the light in the pupil of the subject's eye E, an amount of the incident light per unit area at the pupil of the subject's eye E decreases compared to the case that the reflective surface of the optical scanner 142Y is arranged at the position optically conjugate with the pupil of the subject's eye E. In this way, by daring to generate the pupil aberration, the amount of the incident light per unit area decrease, and an amount of light (a measurement light LS) capable of entering the eye can be increased, the light being generated by the interference optical system 150 to be hereinafter described.

Note that the case has been described in which the optical scanner 142 deflects light two-dimensionally, but the optical scanner 142 may deflect light one-dimensionally. In this case, the optical scanner 142 includes either one of the optical scanner 142X and the optical scanner 142Y.

The interference optical system 150 includes an optical system for acquiring OCT images of the subject's eye E. The optical system has the same configuration as with the conventional swept source OCT apparatus. More specifically, the optical system is an interference optical system that splits the light from the wavelength tunable type (wavelength scanning type) light source into the measurement light and a reference light, make the measurement light returning from the subject's eye E and the reference light having traveled through a reference optical path interfere with each other to generate interference light, and to detect the interference light. The interference optical system obtains a signal representing the spectrum of the interference light as the detection result (detection signal) of the interference light. Incidentally, the interference optical system 150 is not configured according to swept-source OCT, but may be configured according to a conventional spectral-domain OCT.

The OCT light source 151 is a wavelength tunable type (i.e., a wavelength scanning type) light source capable of sweeping (scanning) the wavelengths of the OCT light (emitted light). A laser light source including a resonator and emitting light beam having a center wavelength of 1050 nm, for example, is used as the wavelength tunable type light source. The OCT light source 151 temporally changes the output wavelength in the near infrared wavelength band which cannot be visually recognized by the human eye.

Light L0 output from the OCT light source 151 is guided by an optical fiber f1 to a fiber coupler 152, and divided into the measurement light LS and the reference light LR.

The reference light LR is guided to a fiber emitting end c1 by an optical fiber f2, and a collimator lens 156 is irradiated with the reference light LR emitted from the fiber emitting end c1. The reference light LR emitted from the fiber emitting end c1 is collimated into a parallel light flux by the collimator lens 156. The reference light LR, which has become a parallel light flux, is guided to the prism 154. The prism 154 changes the traveling direction of the reference light LR that has been made into the parallel light flux by the collimator lens 156 in the opposite direction. The optical path of the reference light LR incident on the prism 154 and the optical path of the reference light LR emitted from the prism 154 are parallel. The prism 154 is movable in a direction along the incident light path and the emitting light path of the reference light LR by means of a moving mechanism (not illustrated, a moving mechanism 154D to be hereinafter described). In this case, the moving mechanism is provided with an actuator that generates a driving force for moving the moving mechanism, and a transmission mechanism that transmits the driving force from the actuator to the moving mechanism. The actuator may be a pulse motor. The transmission mechanism may include a combination of gears, and a rack and pinion. As a result, the length of the optical path of the reference light LR is changed.

The reference light LR that has traveled through the prism 154 is converted from the parallel light flux to the convergent light beam by a collimator lens 157 and enters a fiber entrance end c2 of an optical fiber f3, and is guided to a fiber coupler 153 by the optical fiber f3. Incidentally, an optical path length correction member or a dispersion compensation member is arranged between the collimator lens 156 or 157 and the prism 154. The optical path length correction member functions as a delaying means for matching the optical path length (i.e., optical distance) of the reference light LR with the optical path length of the measurement light LS. The dispersion compensation member functions as a dispersion compensation means for matching the dispersion characteristics between the reference light LR and the measurement light LS.

On the other hand, the measurement light LS generated by the fiber coupler 152 is guided to a fiber end c3 by an optical fiber f4. The fiber end c3 is arranged at the fundus conjugate position P. The collimator lens 143 is irradiated with the measurement light LS guided to the fiber end c3. The measurement light LS emitted from the fiber end c3 is collimated into a parallel light flux by the collimator lens 143. The measurement light LS collimated into a parallel light flux reaches the dichroic mirror DM2 via the optical scanner 142 and the focusing lens 141. The measurement light LS is reflected by the dichroic mirror DM2, refracted by the objective lens system 110, and the subject's eye E is irradiated with the measurement light LS. The measurement light LS is scattered (and reflected) at various depth positions of the subject's eye E. The return light of the measurement light LS including such backscattered light advances through the same path as the outward path in the opposite direction and is led to the fiber coupler 152, and then reaches the fiber coupler 153 through an optical fiber f5.

The fiber coupler 153 generates the interference light by superposing the measurement light LS incident through the optical fiber f5 and the reference light LR incident through the optical fiber f3 with each other (i.e., by making the measurement light LS incident through the optical fiber f5 and the reference light LR incident through the optical fiber f3 interfere with each other). The fiber coupler 153 generates a pair of interference light LC by splitting the interference light generated from the measurement light LS and the reference light LR at a predetermined splitting ratio (for example, 1:1). The pair of interference light LC output from the fiber coupler 153 is guided to the detector 155.

The detector 155 is, for example, a balanced photodiode that includes a pair of photodetectors for respectively detecting the pair of interference light LC and outputs the difference between the pair of detection results obtained by the pair of photodetectors. The detector 155 sends the detection result (detection signal) to an unillustrated data acquisition system (DAQ). The DAQ is fed with a clock from the OCT light source 151. The clock is generated in the OCT light source 151 in synchronization with the output timing of each wavelength sweeping (i.e., wavelength scanning) within a predetermined wavelength range performed by the wavelength tunable type light source. The DAQ performs the sampling of the detection result obtained by the detector 155 based on the clock, and send it to an image forming part described later and the like. The image forming part applies Fourier transform and the like to the spectral distribution based on the detection result obtained by the detector 155, for example, with respect to a series of wavelength scans (for each A-line) to form the reflection intensity profile in each A-line. In addition, the image forming part forms image data by applying imaging processing to the reflection intensity profiles of the respective A lines.

[Processing System]

Figure 3:
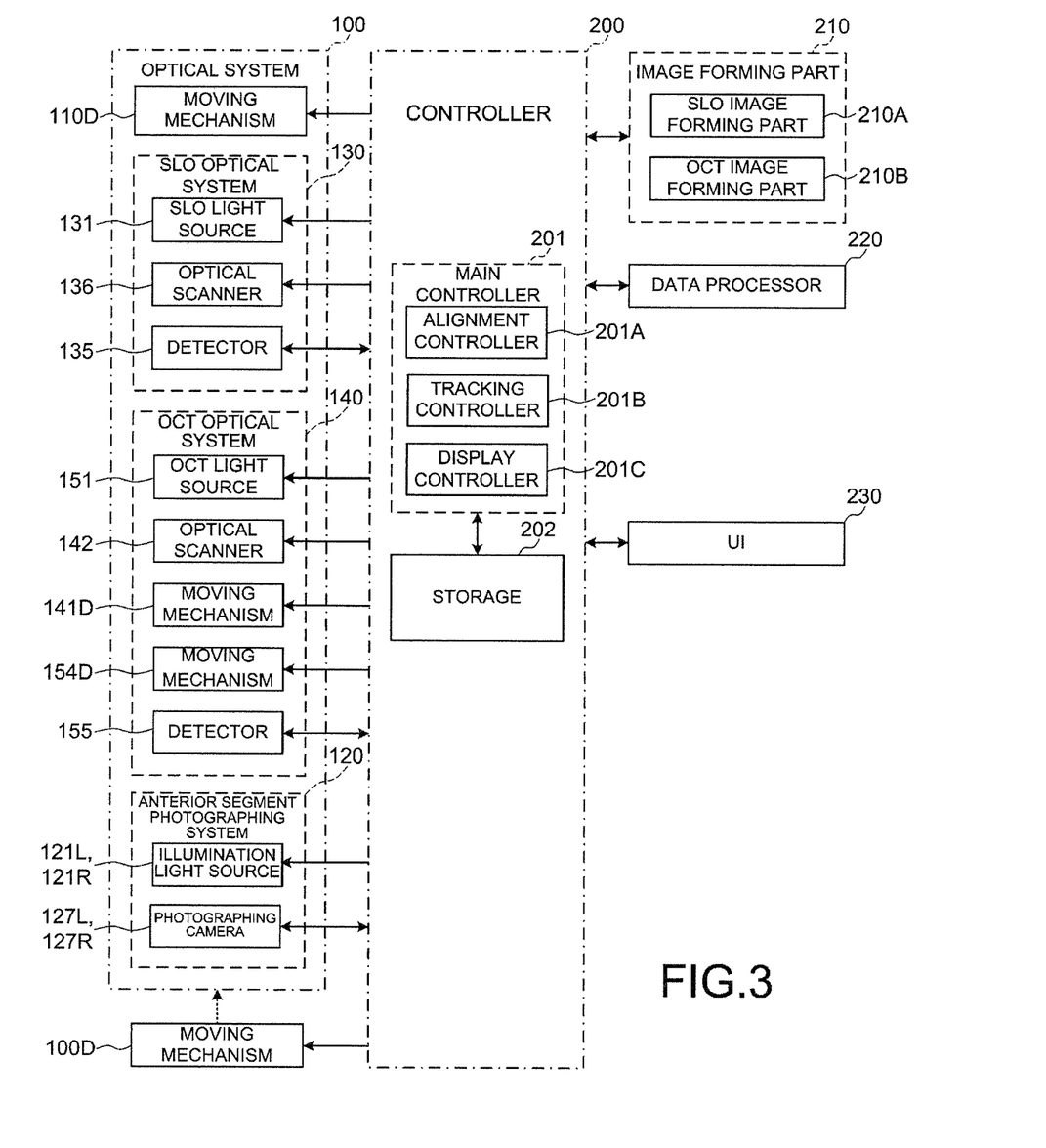
FIG. 3 is a schematic diagram illustrating an example of the configuration of a processing system of the ophthalmologic apparatus according to the embodiments.

FIG. 3 illustrates an example of the configuration of a processing system of the ophthalmologic apparatus according to some embodiments. In FIG. 3, like reference numerals designate like parts as in FIGS. 1 and 2. The same description may not be repeated.

(Controller)

The controller 200 is the center of the processing system of the ophthalmologic apparatus of some embodiments. The controller 200 controls each part of the ophthalmologic apparatus. The controller 200 includes a main controller 201 and a storage 202. The functions of the main controller 201 is implemented by a processor, for example. The storage 202 stores, in advance, a computer program for controlling the ophthalmologic apparatus. The computer program includes, for example, various light source control programs, optical scanner control program, various detector control programs, anterior segment photographing camera control program, image forming program, data processing program, program for user interface, and the like. The processor operates according to the computer programs, and thereby the controller 200 performs the control process.

In the present specification, the term "processor" is used to mean, for example, a circuity including a central processing unit (CPU), a graphics processing unit (GPU), an application specific integrated circuit (ASIC), a programmable logic device (e.g., a simple programmable logic device (SPLD), a complex programmable logic device (CPLD), or a field programmable gate array (FPGA)), or the like. The processor realizes the function according to the embodiment, for example, by read out a computer program stored in a storage circuit or a storage device and executing the computer program.

Examples of the control of the objective lens system 110 includes control of the moving mechanism 110D that moves the objective lens system 110 along the optical axis O, and the like. For example, the moving mechanism 110D is provided with an actuator that generates a driving force for moving the moving mechanism 110D and a transmission mechanism that transmits the driving force from the actuator to the moving mechanism 110D. The actuator may be a pulse motor. The transmission mechanism may include a combination of gears, and a rack and pinion. The main controller 201 controls the moving mechanism 110D by sending a control signal to the actuator.

Examples of the control of the SLO optical system 130 include control of the SLO light source 131, control of the optical scanner 136, control of the detector 135, and the like. Examples of the control of the SLO light source 131 includes turning on and off the light source, adjustment of amount of light, adjustment of aperture, and the like. Examples of the control of the optical scanner 136 include control of the scanning position and the scanning area by means of the optical scanner 136X, control of the scanning position and the scanning area by means of the optical scanner 136Y, and the like. Examples of the control of the detector 135 include adjustment of exposure of a detecting element, adjustment of gain of a detecting element, adjustment of detecting rate of a detecting element, and the like.

Examples of the control of the OCT optical system 140 include control of the OCT light source 151, control of the optical scanner 142, control of the moving mechanism 141D and the moving mechanism 154D, control of the detector 155, and the like. Examples of the control of the OCT light source 151 includes turning on and off of the light source, adjustment of amount of light, adjustment of aperture, and the like. Examples of the control of the optical scanner 142 include control of the scanning position and the scanning area by means of the optical scanner 142X, control of the scanning position and the scanning area by means of the optical scanner 142Y, and the like. The moving mechanism 141D moves the focusing lens 141 along the optical path of the OCT optical system 140. For example, the moving mechanism 141D is provided with an actuator that generates a driving force for moving the moving mechanism 141D and a transmission mechanism that transmits the driving force from the actuator to the moving mechanism 141D. The actuator may be a pulse motor. The transmission mechanism may include a combination of gears, and a rack and pinion. The main controller 201 controls the moving mechanism 141D by sending a control signal to the actuator. The moving mechanism 154D moves the prism 154 in a direction along the incident light path and the emitting light path of the reference light LR. For example, the moving mechanism 154D is provided with an actuator that generates a driving force for moving the moving mechanism 154D and a transmission mechanism that transmits the driving force from the actuator to the moving mechanism 154D. The actuator may be a pulse motor. The transmission mechanism may include a combination of gears, and a rack and pinion. The main controller 201 controls the moving mechanism 154D by sending a control signal to the actuator. Examples of the control of the detector 155 include adjustment of exposure of a detecting element, adjustment of gain of a detecting element, adjustment of detecting rate of a detecting element, and the like.

Examples of the control of the anterior segment photographing system 120 include control of the anterior segment illumination light sources 121L and 121R, control of the anterior segment photographing cameras 127L and 127R, and the like. The control of the anterior segment illumination light sources 121L and 121R include turning on and off the light sources, adjustment of the amount of light, adjustment of apertures, and the like. The control of the anterior segment photographing cameras 127L and 127R include adjustment of exposure of the imaging devices, adjustment of gain of the imaging devices, adjustment of photographing rate of the imaging devices, and the like.

Examples of the control of the optical system 100 (including the dichroic mirror DM1 and the anterior segment photographing system 120) include control of the moving mechanism 100D that moves the optical system 100 in the X direction, the Y direction, and the Z direction, and the like. For example, the moving mechanism 100D is provided with an actuator that generates a driving force for moving the moving mechanism 100D and a transmission mechanism that transmits the driving force from the actuator to the moving mechanism 100D. The actuator may be a pulse motor. The transmission mechanism may include a combination of gears, and a rack and pinion. The main controller 201 controls the moving mechanism 100D by sending a control signal to the actuator.

The main controller 201 includes an alignment controller 201A, a tracking controller 201B, and a display controller 201C.

The alignment controller 201 A controls the perform of the alignment for position matching of the optical system 100 (the objective lens system 110) with respect to the subject's eye E. The alignment controller 201A can control the perform of the alignment as below, based on the two anterior segment images substantially simultaneously acquired by the anterior segment photographing cameras 127L and 127R.

(First Example of Alignment Control)

As the first example of the alignment control, the alignment controller 201A can control the moving mechanism 100D or the moving mechanism 110D so that a position relationship between a current position of the optical system 100 or the objective lens system 110 and a three-dimensional position of the eye E becomes a predetermined positional relationship. In particular, the alignment controller 201A controls the moving mechanism 100D or the moving mechanism 110D so that the optical axis of the optical system 100 or the objective lens system 110 matches the axis of the subject's eye E, and that the distance from the subject's eye E to the objective lens 111 becomes a predetermined working distance.

In the example of the present control, firstly, the alignment controller 201A obtains a current position of the optical system 100 or the objective lens system 110. The alignment controller 201A can obtain the current position of the optical system 100 from control contents of the moving mechanism 100D controlled by means of the main controller 201. The alignment controller 201A can obtain the current position of the objective lens system 110 (the objective lens 111) from control contents of the moving mechanism 110D controlled by means of the main controller 201. Besides, the alignment controller 201A may obtain the current position of the optical system 100 or the objective lens system 110 based on the detection result obtained from an unillustrated position sensor. The alignment controller 201A controls a data processor 220, the data processor 220 having a function as a position identifying part, to calculate the three-dimensional position of the subject's eye E. The alignment controller 201A controls the moving mechanism 100D or the moving mechanism 110D so as to become the above position relationship, based on the obtained current position of the optical system 100 or the objective lens system 110 and the calculated three-dimensional position of the subject's eye E.

The detail of the alignment control such the first example of the alignment control is disclosed in, for example, Japanese Unexamined Patent Application Publication No. 2013-248376.

(Second Example of Alignment Control)

In the second example of the alignment control, two partial images of the two anterior segment images substantially simultaneously obtained by the anterior segment photographing cameras 127L and 127R are used. The display controller 201C described later displays the two partial images on an alignment screen (e.g., a screen of the display device of an User Interface (UI) 230). The alignment controller 201A can control the moving mechanism 100D or the moving mechanism 110D so that two display positions of the two partial images in the alignment screen coincide with predetermined target position(s) and a position relationship of the two partial images becomes a predetermined position relationship. Examples of the two partial images include images of different parts each other in the two anterior segment images. For example, the two partial images are a first partial image and a second partial image, the first partial image being rendered the upper half of a pupil region in the anterior segment image obtained by the anterior segment photographing camera 127L, the second partial image being rendered the bottom half of a pupil region in the anterior segment image obtained by the anterior segment photographing camera 127R. The target position(s) may be predetermined position(s), or the target position(s) may be position(s) in the anterior segment image(s) specified using the user interface 230.

When the optical system 100 or the objective lens system 110 is moved in the XY direction by the moving mechanism 100D or the moving mechanism 110D, the first partial image and the second partial image in the alignment screen are displaced as one in a direction corresponding to the moving direction of the optical system 100 and the like. The alignment controller 201A controls the moving mechanism 100D or the moving mechanism 110D so as to cancel a displacement of the display positions of the first partial image and the second partial image with respect to the predetermined target position(s) in the alignment screen. Thereby, the optical axis of the optical system 100 or the objective lens system 110 is changed so as to match the axis of the subject's eye E.

Besides, when the optical system 100 or the objective lens system 110 is moved in the Z direction by the moving mechanism 100D or the moving mechanism 110D, along the change in positions of the anterior segment photographing cameras 127L and 127R with respect to the subject's eye E, the first partial image and the second partial image are relatively and transversely displaced each other. The alignment controller 201A controls the moving mechanism 100D or the moving mechanism 110D so as to cancel a relative and transverse displacement of the first partial image and the second partial image and form an image representing a single pupil region. Thereby, the distance from the objective lens 111 and the subject's eye E is changed so as to become the predetermined working distance.

In the example of the present control, firstly, the alignment controller 201A controls the data processor 220 to specify the pupil region as a characteristic region of each the two anterior segment images obtained by the anterior segment photographing cameras 127L and 127R. The alignment controller 201A controls the data processor 220 to generate two partial images by vertically dividing the specified pupil region. The alignment controller 201A controls the moving mechanism 100D or the moving mechanism 110D based on a moving direction and a moving distance corresponding to a displacement of the display position(s) of the first partial image and the second partial image with respect to the target position(s) in the alignment screen. Thereby, the optical system 100 or the objective lens system 110 is moved in at least one of the X direction and the Y direction. Moreover, the alignment controller 201A controls the moving mechanism 100D or the moving mechanism 110D base on a moving direction and a moving distance corresponding to a relative and transverse displacement between the pupil region of the first partial image and the pupil region of the second partial image. Thereby, the optical system 100 or the objective lens system 110 is moved in the Z direction.

The detail of the alignment control such the second example of the alignment control is disclosed in, for example, Japanese Unexamined Patent Application Publication No. 2014-200678, Japanese Unexamined Patent Application Publication No. 2014-200679, and Japanese Unexamined Patent Application Publication No. 2014-200680.

The tracking controller 201B controls the perform of the tracking for the SLO image of the subject's eye E obtained by the SLO optical system 130. For example, the tracking controller 201B specifies a characteristic site of the SLO image at a predetermined timing, and when a position of the specified site is changed, the tracking controller 201B obtains an amount of moving so as to cancel an amount of displacement of the position. The tracking controller 201B controls the perform of the tracking for the SLO image based on the obtained the amount of moving.

Moreover, the tracking controller 201B controls the perform of the tracking for the OCT image of the subject's eye E based on the SLO image, the OCT image being obtained by the OCT optical system 140. For example, the tracking controller 201B specifies a characteristic site of the SLO image at a predetermined timing, and when a position of the specified site is changed, the tracking controller 201B obtains an amount of moving so as to cancel an amount of displacement of the position. The tracking controller 201B controls the perform of the tracking for the OCT image based on the obtained amount of moving. The data processor 220 may be provided with the tracking controller 201B.

The display controller 201C displays various kinds of information on the user interface 230 described later. Examples of the information displayed on the user interface 230 include information generated by the controller 200, image (the anterior segment image, the SLO image, the OCT image, or the like.) formed by the image forming part 210, information after data processing of the data processor 220, and the like. Examples of the information after data processing of the data processor 220 include the above first partial image, the above second partial image, and the like.

(Image Forming Part)

The image forming part (image former) 210 include an SLO image forming part 210A and an OCT image forming part 210B. The SLO image forming part 210A forms image data of the SLO image based on the detection signal received from the detector 135 and a pixel position signal received from the controller 200. The OCT image forming part 210B forms image data of the OCT image (the tomographic image of the fundus Ef and the like) based on the detection signal received from the detector 155 and a pixel position signal received from the controller 200. Moreover, the image forming part 210 forms the two anterior segment images by photographing from different directions each other based on the detection result of the reflection light from the anterior segment of the subject's eye E obtained by the imaging devices of the anterior segment photographing cameras 127L and 127R. The various images (the various image data) generated by the image forming part 210 are stored in the storage 202, for example.

(Data Processer)

A data processor 220 performs various types of data processing. As the data processing, for example, the data processor 220 performs processing on image data formed by the image forming part 210 or another device. Examples of the processing include various types of image processing, analyzing processing of image, and diagnosis support processing such as image evaluation based on the image data.

In the case that alignment controller 201A controls the alignment control shown in the above the first example of the alignment control, the data processor 220 includes a position specifying part at least. Further, the data processor 220 includes an image correction part. The image correction part corrects distortion of each photograph images captured by the anterior segment photographing cameras 127L and 127R based on the aberration information stored in the storage 202 or an unillustrated storage unit. This process may be performed by, for example, known image processing technology based on a correction factor for correcting distortion aberration.

The position specifying part includes a characteristic position specifying part and a three-dimensional position calculating part. The characteristic position specifying part specifies a characteristic position corresponding to a predetermined characteristic site (e.g., pupil) of each photograph images obtained by the anterior segment photographing cameras 127L and 127R. The characteristic position specifying part specifies the pupil region by searching an image region with low luminance utilizing the fact that the pupil is rendered with lower luminance than other sites, and specifies the center position or the position of the center of gravity of the specified pupil region as the characteristic position. The three-dimensional position calculating part calculates the three-dimensional position of the subject's eye E based on the positions of the anterior segment photographing cameras 127L and 127R and the characteristic positions in the two photograph images specified by the characteristic position specifying part. The three-dimensional position calculating part applies known trigonometry to the positions of the two anterior segment photographing cameras 127L and 127R (these are known) and the specified characteristic positions, thereby calculating the three-dimensional position of the subject's eye E.

In the case that alignment controller 201A controls the alignment control shown in the above the second example of the alignment control, the data processor 220 include a characteristic region specifying part, a partial image generating part, and a displacement calculating part. The characteristic region specifying part analyzes each photograph images captured by the anterior segment photographing cameras 127L and 127R to specify a characteristic region corresponding to the pupil in each of the photograph images. The characteristic region specifying part can specify the pupil region by the searching an image region with low luminance utilizing the fact that the pupil is rendered with lower luminance than other sites. The partial image generating part analyzes each photograph images captured by the anterior segment photographing cameras 127L and 127R to specify the center positions or the positions of the center of gravity of the pupil regions specified by the characteristic region specifying part. The partial image generating part forms a partial image rendered the upper half than the horizontal line passing through the specified center position or the specified position of the center of gravity and a partial image rendered the bottom half than the horizontal line. The displacement calculating part obtains the displacement of the display positions of the first partial image and the second partial image with respect to the predetermined target position(s) in the alignment screen and the relative and traverse displacement of the first partial image and the second partial image.

The functions of at least one of the image forming part 210 and the data processor 220 are implemented by the processor, for example. The storage 202 or an unillustrated storage stores, in advance, a computer program for implementing the functions of at least one of the image forming part 210 and the data processor 220. The computer programs include a program for forming image and a program for data processing. The processor operates according to the computer programs, and thereby the image forming part 210 and the data processor 220 perform the above processing.

(User Interface)

The user interface 230 has a function for interchanging information between the user and the ophthalmologic apparatus. The user interface 230 includes a display device and an operation device (input device). The display devices may include a display part, and it may include another display device. The operation device includes various hardware keys and/or software keys. In response to operation information based on user's operation on the operation device, the controller 200 can output a control signal corresponding to the operation content to each part of the ophthalmologic apparatus. At least part of the display device and at least part of the operation device may be configured integrally. One example of this is the touch panel display.

The optical system 100, the SLO optical system 130 or the OCT optical system 140, and the image forming part 210 are examples of the "data acquisition system" according to the embodiment. The relay lenses 123L, 123R, 124L, and 124R, the diaphragms 125L and 125R, the imaging lenses 126L and 126R, and the anterior segment photographing cameras 127L and 127R are examples of the "pair of the optical system" according to the embodiment. The anterior segment photographing cameras 127L and 127R are examples of the "photographing apparatus" according to the embodiment. The relay lenses 123L and 124L, and the relay lenses 123R and 124R are examples of the "relay optical system" according to the embodiment. The diaphragms 125L and 125R are examples of the "light flux limiting element that limits light flux" according to the embodiment. The imaging lenses 126L and 126R are examples of the "lens that guides the light flux to a photographing apparatus" according to the embodiment. The dichroic mirror DM1 is an example of the "optical path coupling member" according to the embodiment. The anterior segment illumination light sources 121L and 121R, and the collimator lenses 122L and 122R are examples of the "anterior segment illumination system" according to the embodiment. The data processor 220 is an example of the "position specifying part" according to the embodiment. The optical system 100, the SLO optical system 130, or the OCT optical system 140 is examples of the "scan optical system" according to the embodiment.

[Operation]

The operation of the ophthalmologic apparatus according to some embodiments will be described.

Figure 4:
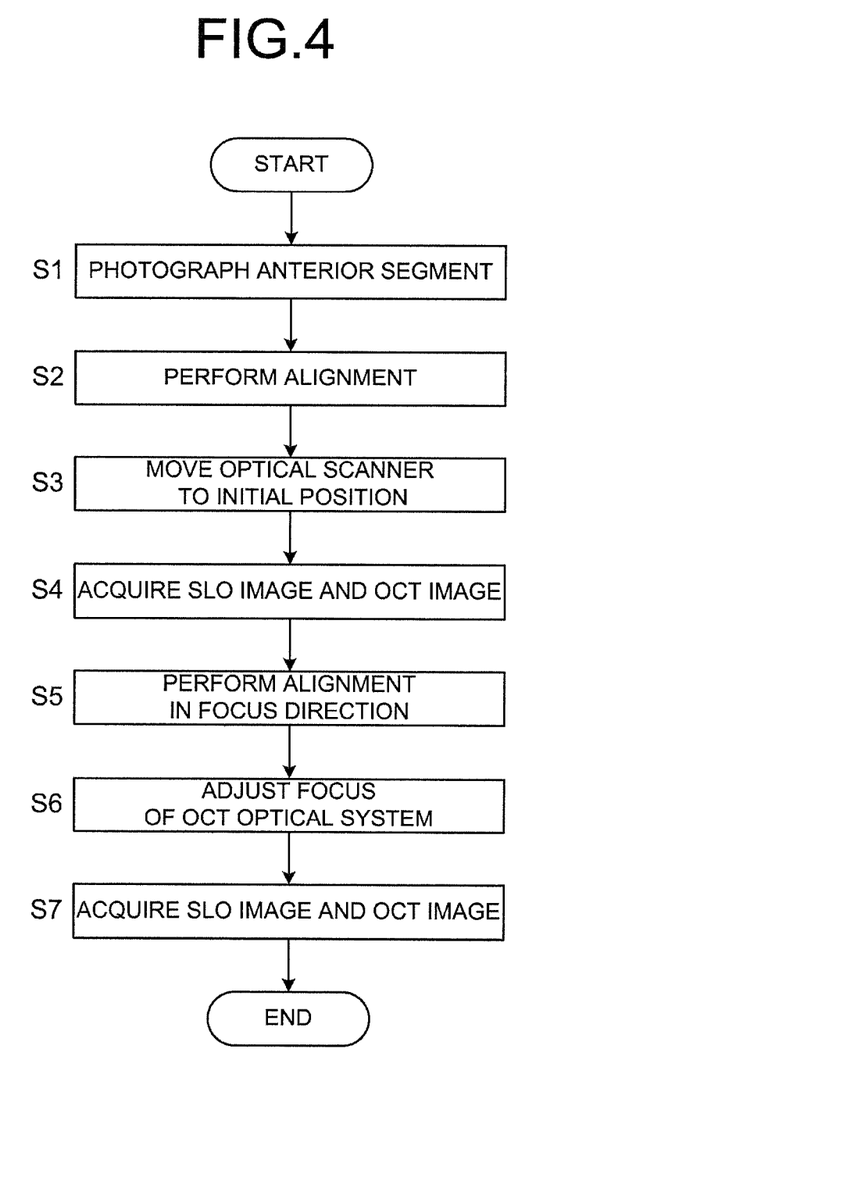
FIG. 4 is a flow chart of an operation example of the ophthalmologic apparatus according to the embodiments.

FIG. 4 shows an example of the operation of the ophthalmologic apparatus according to some embodiments.

(S1)

Firstly, the controller 200 controls the anterior segment photographing system 120 to acquire anterior segment images of the subject's eye E. Thereby, the two anterior segment images captured from different directions by the anterior segment photographing cameras 127L and 127R are obtained.

(S2)

The alignment controller 201A controls the moving mechanism 100D based on the two anterior segment images acquired in the step S1, thereby performing the position matching of the optical system 100 and the objective lens system 110 with respect to the subject's eye E (in the X direction, the Y direction, and the Z direction). For example, the alignment controller 201A controls the moving mechanism 100D based on the current position of the optical system 100 and the three-dimensional position of the subject's eye E specified based on the two anterior segment images so as to match the optical axis of the optical system 100 with the axis of the subject's eye E, and such that the distance of the optical system 100 with respect to the subject's eye E becomes the predetermined working distance (the first example of the alignment control). Besides, for example, the alignment controller 201A controls the moving mechanism 100D such that the display positions in the alignment screen coincide with predetermined target position(s), the display positions being the position of the partial image of the upper half generated from one of the two anterior segment images and the position of the partial image of the bottom half generated from the other of the two anterior segment images, and so as to form the image representing the single pupil region by cancelling the relative and traverse displacement of the two partial images (the second example of the alignment control).

(S3)

The controller 200 moves each of the optical scanner 136 and 142 to a predetermined initial position.

(S4)

The controller 200 turns on the SLO light source 131 and controls the optical scanner 136 to start scanning the fundus Ef of the subject's eye E with the light from the SLO light source 131. The SLO image forming part 210A forms the SLO image of the fundus Ef based on the detection result of the fundus reflection light obtained by the detector 135. Moreover, the controller 200 turns on the OCT light source 151 and controls the optical scanner 142 to start scanning the fundus Ef of the subject's eye E with the measurement light LS based on the light emitted from the OCT light source 151. The OCT image forming part 210B forms an OCT image of the fundus Ef based on the detection result of the interference light obtained by the detector 155. In the step S4, the tracking controller 201B may start the tracking control for the SLO image and the tracking control for the OCT image.

(S5)

The alignment controller 201A performs alignment in the focus direction of the retina based on the anterior segment image obtained by the anterior segment photographing system 120 or the SLO image obtained in the step S4. Thereby, it becomes possible to finely adjust the position of the objective lens system 110 in the optical axis O direction.

(S6)

Based on the detection signal of the interference light obtained by the OCT optical system 140, the main controller 201 changes the focus position of the OCT optical system 140. The main controller 201 changes the focus position of the OCT optical system 140, for example, by controlling the moving mechanism 141D so that the amplitude of the detection signal of a predetermined interference light becomes maximum.

(S7)

Once again, by controlling the optical scanner 136, the main controller 200 starts scanning the fundus Ef of the subject's eye E with the light emitted from the SLO light source 131. The SLO image forming part 210A forms an SLO image of the fundus Ef based on the detection result of the fundus reflection light obtained by the detector 135. Moreover, once again, by controlling the optical scanner 142, the controller 200 starts scanning the fundus Ef of the subject's eye E with the measurement light LS based on the light emitted from the OCT light source 151. The OCT image forming part 210B forms an OCT image of the fundus Ef based on the detection result of the interference light obtained by the detector 155. This terminates the operation of the ophthalmologic apparatus (END).

In the embodiment, an example is described in which the photograph images of the anterior segment of the subject's eye E are obtained by the two imaging device included in the anterior segment photographing cameras 127L and 127R; however, the configuration of the ophthalmologic apparatus of the embodiment is not limited to this. For example, the function of the anterior segment photographing cameras 127L and 127R can be implemented by a single anterior segment photographing camera. In this case, return light of the illumination light from the anterior segment of the subject's eye E is converged on a first detection region in the detector plane of an imaging device included in the single anterior segment photographing camera by means of the imaging lens 126L, and is converged on a second detection region in the detector plane by means of the imaging lens 126R.

[Modification]

In the embodiment, the case has been described in which the anterior segment of the subject's eye E is obtained by the imaging device of each of the pair of optical systems included in the anterior segment photographing system 120. However, the configuration of the ophthalmologic apparatus according to the embodiment is not limited thereto. Hereinafter, an ophthalmologic apparatus according to the modification of the embodiment will be described focusing on differences from the embodiment.

Figure 5:
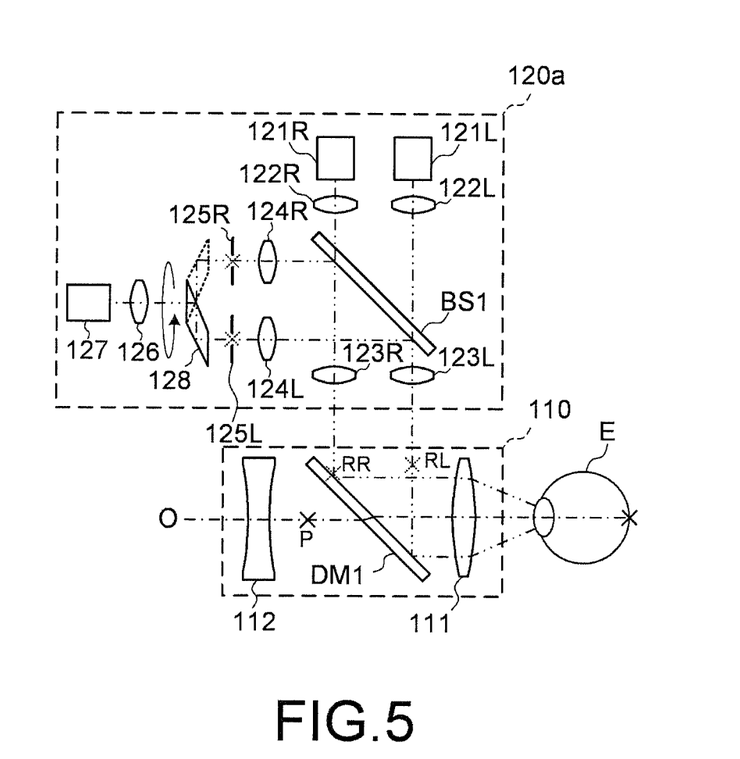
FIG. 5 is a schematic diagram illustrating an example of the configuration of an optical system of the ophthalmologic apparatus according to a modification of the embodiments.

FIG. 5 illustrates an example of the configuration of the optical system of the ophthalmologic apparatus according to the modification of some embodiments. In FIG. 5, components similar to those in FIG. 2 are given the same reference numerals. The description of such components is basically omitted.

The configuration of an anterior segment photographing system 120a of the modification is different from the configuration of the anterior segment photographing system 120 in that: an anterior segment photographing camera 127 is provided in place of the anterior segment photographing cameras 127L and 127R; an imaging lens 126 is provided in place of the imaging lenses 126L and 126R; and a rhomboid prism 128 is additionally provided between the imaging lens 126 and the diaphragms 125L and 125R. The rhomboid prism 128 is an optical member for moving an optical axis in parallel. The rhomboid prism 128 is rotated around an axis parallel to a lens optical axis of the imaging lens 126 by an unillustrated moving mechanism (a moving mechanism 128D described later). That is, the rhomboid prism 128 selectively guides the optical paths of the pair of optical systems included in the anterior segment photographing system 120a to the detector plane of the anterior segment photographing camera 127. Thereby, an optical axis is displaced so that the lens optical axis of the relay lens 124L coincides with the lens optical axis of the imaging lens 126, or so that the lens optical axis of the relay lens 124R coincides with the lens optical axis of the imaging lens 126. Therefore, the return light of the illumination light passing through the opening formed in the diaphragm 125L and the return light of the illumination light passing through the opening formed in the diaphragm 125R are alternately converged on the detector plane of the imaging device included in the anterior segment photographing camera 127.

Figure 6:
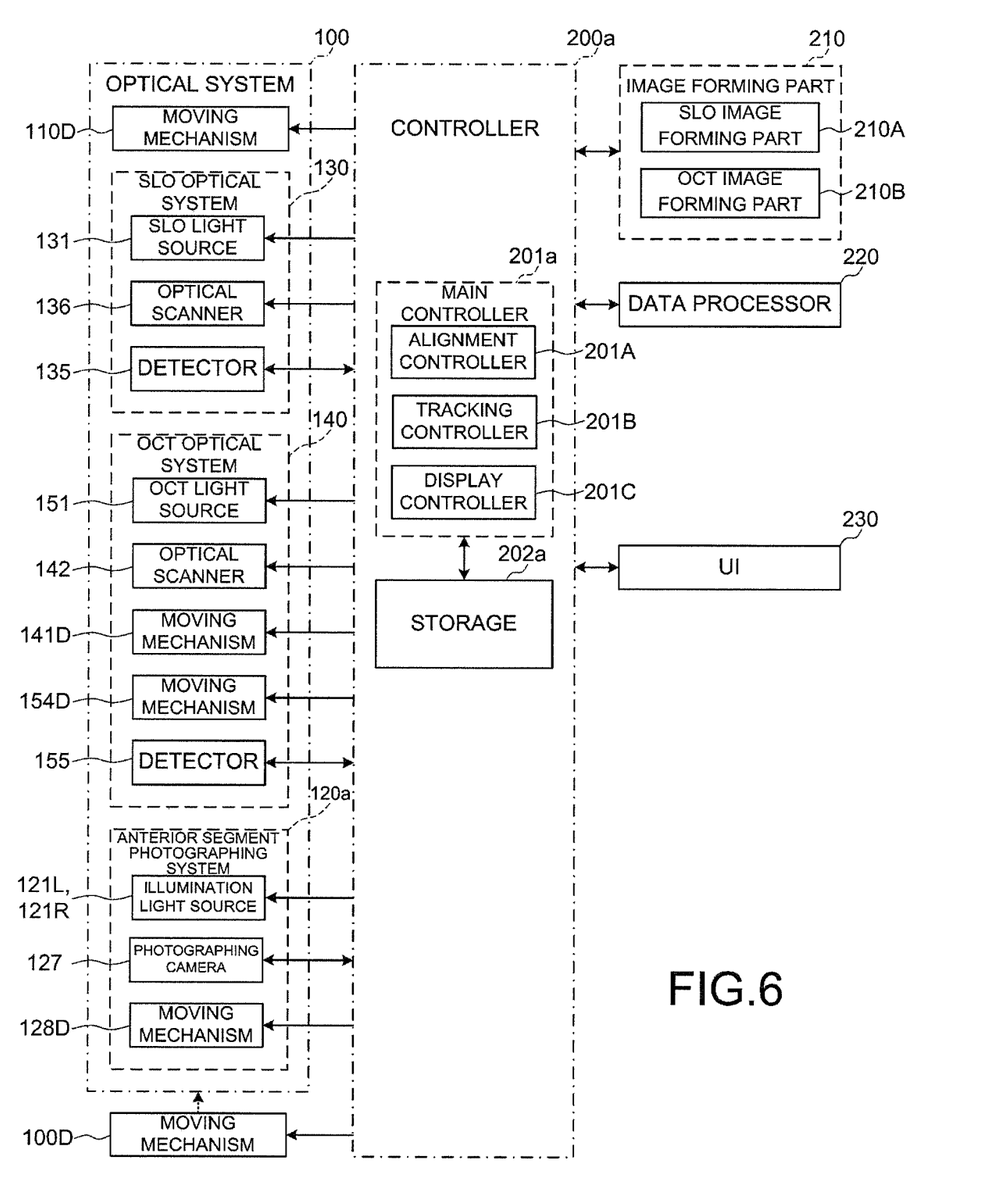
FIG. 6 is a schematic diagram illustrating an example of the configuration of a processing system of the ophthalmologic apparatus according to the modification of the embodiments.

FIG. 6 illustrates an example of the configuration of the processing system of the ophthalmologic apparatus according to the modification of some embodiments. In FIG. 6, components similar to those in FIG. 3 are given the same reference numerals. The description of such components is basically omitted.

The controller 200a is the center of the processing system of the ophthalmologic apparatus of the modification. The controller 200a is different from the controller 200 of the embodiment in that: the controller 200a controls the anterior segment photographing camera 127 in place of the anterior segment photographing cameras 127L and 127R; and the controller 200a newly controls the moving mechanism 128D. The moving mechanism 128D rotates the rhomboid prism 128 around the axis parallel to the lens optical axis of the imaging lens 126. For example, the moving mechanism 128D is provided with an actuator that generates a driving force for moving mechanism 128D, and a transmission mechanism that transmits the driving force from the actuator to the moving mechanism 128D. The actuator may be a pulse motor. The transmission mechanism may include a combination of gears, and a rack and pinion. The main controller 201a controls the moving mechanism 128D by sending a control signal to the actuator.

The main controller 201a included in the controller 200a can control the photographing of the anterior segment by means of the anterior segment photographing camera 127 at a photographing timing synchronized with the rotation of the rhomboid prism 128 by means of the moving mechanism 128D. Thereby, the anterior segment image based on the return light of the illumination light passing through the opening formed in the diaphragm 125L and the return light of the illumination light passing through the opening formed in the diaphragm 125R can be alternately obtained. It is possible to obtain the two photograph images captured from different directions by the pair of optical systems included in the anterior segment photographing system 120a substantially simultaneously, by controlling a rotation speed of the rhomboid prism 128.

The anterior segment photographing camera 127 is an example of the "photographing apparatus" according to the embodiment. The rhomboid prism 128 is an example of the "optical path selecting member" according to the embodiment.

[Effects]

The effects of the ophthalmologic apparatus according to the embodiment or the modification will be described.

The ophthalmologic apparatus according some embodiments includes an objective lens (111), a data acquisition system (the optical system 100, the SLO optical system 130 or the OCT optical system 140, and the image forming part 210), and an anterior segment photographing system (120, 120a). The data acquisition system is configured to acquire data of a subject's eye (E) optically via the objective lens. The anterior segment photographing system includes a pair of optical systems (the relay lenses 123L, 123R, 124L, and 124R, the diaphragms 125L and 125R, the imaging lenses 126L and 126R, and the anterior segment photographing cameras 127L and 127R) for photographing an anterior segment of the subject's eye from different directions via the objective lens.

According to such a configuration, it is possible to obtain a pair of photograph images by photographing the anterior segment of the subject's eye from different directions via the objective lens by means of the pair of the optical systems. This make it enable to observe in stereo to grasp the state of the anterior segment of the subject's eye in detail using the obtained pair of the photograph images.

Besides, in the ophthalmologic apparatus according to some embodiments, each of the pair of the optical systems may include a light flux limiting element (the diaphragm 125L or 125R) and a lens (the imaging lens 126L or 126R). The light flux limiting element limits light flux incident through the objective lens. The lens guides the light flux passing through the light flux limiting element to a photographing apparatus (the anterior segment photographing camera 127L or 127R).

According such a configuration, it is possible to observe the anterior segment of the subject's eye in stereo with the desired field of view, the desired brightness, and the desired contrast by arranging the light flux limiting element at a position corresponding to an effective lens diameter of the objective lens.

Besides, in the ophthalmologic apparatus according to some embodiments, each of the pair of the optical systems may further include a relay optical system (the relay lenses 123L and 124L or the relay lens 123R and 124R). The relay optical system is configured to form a point (RR, RL) optically conjugate with the light flux limiting element between the objective lens and the light flux limiting element.

According such a configuration, the point optically conjugate with the light flux limiting element is formed between the objective lens and the light flux limiting element by the relay optical system. This makes it enable to arranging the pair of the optical systems for photographing the anterior segment of the subject's eye from different directions side by side. Therefore, it becomes possible to secure a sufficient field of vision. In addition, because it becomes possible to secure the stereo angle sufficiently, observing the anterior segment of the subject's eye E with natural stereoscopic effect similar to that observed with the naked eye becomes possible.

Besides, the ophthalmologic apparatus according to some embodiments may include an optical path coupling member (the dichroic mirror DM1) configured to combine an optical path of the data acquisition system with optical paths of the pair of the optical systems. The point of at least one of the pair of the optical systems may be located in the vicinity of an optical path coupling surface of the optical path coupling member.

According to such a configuration, it becomes possible to arrange the pair of the optical systems for photographing the anterior segment of the subject's eye side by side, while coupling the optical path of the data acquisition system with the optical paths of the pair of the optical systems.

Besides, the ophthalmologic apparatus according to some embodiments may include an optical path selecting member (the rhomboid prism 128) for selectively guiding the optical paths of the pair of the optical systems to an imaging surface of the photographing apparatus.

According to such a configuration, the pair of photograph images obtained by photographing the anterior segment of the subject's eye from different directions can be acquired with a single photographing apparatus.

Besides, the ophthalmologic apparatus according to some embodiments may include an anterior segment illumination system (the anterior segment illumination light source 121L and 121R, the collimator lens 122L and 122R) configured to illuminate the anterior segment via the objective lens.

According to such a configuration, it is possible to obtain a pair of photograph images by photographing the anterior segment of the subject's eye illuminated by the anterior segment illumination system via the objective lens from different directions. This make it enable to observe the anterior segment of the subject's eye in stereo using the obtained pair of the photograph images.

Besides, the ophthalmologic apparatus according to some embodiments may include a position specifying part (the data processor 220) that specifies a three-dimensional position of the subject's eye based on a pair of photograph images obtained substantially simultaneously by the pair of the optical systems.

According to such a configuration, the three-dimensional position of the subject's eye is specified from the pair of photograph images obtained by photographing the anterior segment of the subject's eye from different directions via the objective lens by means of the pair of the optical systems. This make it enable to perform the position matching of the data acquisition system with respect to the subject's eye.

Besides, the ophthalmologic apparatus according to some embodiments may include a moving mechanism (100D, 110D) that moves the objective lens and the data acquisition system at least and a controller (200, 200a) configured to control the moving mechanism based on the pair of photograph images obtained substantially simultaneously by the pair the of optical systems.

According to such a configuration, it is possible to perform the position matching of the data acquisition system with respect to the subject's eye from the pair of photograph images obtained by photographing the anterior segment of the subject's eye from different directions via the objective lens by means of the pair of the optical systems.

Besides, in the ophthalmologic apparatus according to some embodiments, the data acquisition system may include a scan optical system (the optical system, the SLO optical system 130, or the OCT optical system 140) configured to scan the subject's eye with light via the objective lens and an image forming part (210) configured to form an image of the subject's eye based on data acquired by the scan optical system.

According to such a configuration, in the ophthalmologic apparatus to obtain an image of the subject's eye by scanning the subject's eye with light via the objective lens, the pair of photograph images is obtained by photographing the anterior segment of the subject's eye from different directions via the objective lens by means of the pair of the optical systems. This make it enable to observe the anterior segment in stereo using the obtained pair of the photograph images.

[Other Modifications]

The above-described some embodiments or the modification are merely an example for carrying out the present invention. Those who intend to implement the present invention can apply any modification, omission, addition, or the like within the scope of the gist of the present invention.

In the above embodiment or the modifications thereof, an example is described in which the alignment control of the optical system 100 (the objective lens system 110) is performed in the X direction, the Y direction, and the Z direction; however, they are not so limited. For example, a controller controls the optical system 100 (the objective lens system 110) to move in the X direction and the Y direction using a pair of the photograph images obtained by a pair of optical systems included in an anterior segment photographing system, and to display an amount of a displacement in the Z direction and a direction of the displacement on the display device of the user interface 230. In the case that the objective lens 111 is a wide-angle lens and the working distance is short, this makes it enable to ensure the safety of the alignment.

In the above embodiment or the modifications thereof, an example of the ophthalmologic apparatus for observing in stereo by the anterior segment photographing system is described; however, they are not so limited. For example, the ophthalmologic apparatus according to some embodiments is provided with an anterior segment observing system in place of the anterior imaging system. The anterior segment observing system is provided with an ocular lens system in place of the anterior segment photographing system.

In the above embodiment or the modifications thereof, an example is described in which the configuration of the objective lens system 110 has the configuration shown in FIG. 1; however, they are not so limited.

The anterior segment photographing system according to some embodiments or the modification includes two or more anterior segment photographing cameras for photographing the anterior segment of the subject's eye form two or more different directions. Even in this case, the alignment controller 201A according to some embodiments can perform the alignment from a parallax obtained based on the two or more photograph images acquired using these anterior segment photographing cameras.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ophthalmologic apparatus comprising:
   an objective lens;
   a data acquisition system configured to acquire data of a subject's eye optically via the objective lens; and
   an anterior segment photographing system that includes a pair of optical systems for substantially simultaneously photographing an anterior segment of the subject's eye from different directions via the objective lens, each of the pair of optical systems including
- a light flux limiting element that limits light flux incident through the objective lens,
- a lens that guides the light flux passing through the light flux limiting element to a photographing apparatus, and
- a relay optical system configured to form a point optically conjugate with the corresponding light flux limiting element between the objective lens and the corresponding light flux limiting element.

2. The ophthalmologic apparatus of claim 1, further comprising:
an optical path coupling member configured to combine an optical path of the data acquisition system with optical paths of the pair of optical systems, wherein the point of at least one of the pair of optical systems is located in the vicinity of an optical path coupling surface of the optical path coupling member.

3. The ophthalmologic apparatus of claim 1, further comprising:
an optical path selecting member for selectively guiding the optical paths of the pair of optical systems to an imaging surface of the photographing apparatus.

4. The ophthalmologic apparatus of claim 1, further comprising:
an anterior segment illumination system configured to illuminate the anterior segment via the objective lens.

5. The ophthalmologic apparatus of claim 1, further comprising:
a position specifying part that specifies a three-dimensional position of the subject's eye based on a pair of photograph images obtained substantially simultaneously by the pair of optical systems.

6. The ophthalmologic apparatus of claim 1, further comprising:
a moving mechanism that moves the objective lens and the data acquisition system at least; and
a controller configured to control the moving mechanism based on the pair of photograph images obtained substantially simultaneously by the pair of optical systems.

7. The ophthalmologic apparatus of claim 1, wherein the data acquisition system includes
a scan optical system configured to scan the subject's eye with light via the objective lens; and
an image forming part configured to form an image of the subject's eye based on data acquired by the scan optical system.

* * * * *